US008648300B2

(12) United States Patent
Isawa et al.

(10) Patent No.: US 8,648,300 B2
(45) Date of Patent: Feb. 11, 2014

(54) CHARGED PARTICLE BEAM APPARATUS

(71) Applicant: Hitachi High-Technologies Corporation, Tokyo (JP)

(72) Inventors: Miki Isawa, Hitachinaka (JP); Minoru Yamazaki, Ushiku (JP); Yuzuru Mizuhara, Naka (JP); Hiroshi Makino, Chino (JP); Hideyuki Kazumi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/939,767

(22) Filed: Jul. 11, 2013

(65) Prior Publication Data

US 2014/0014836 A1  Jan. 16, 2014

(30) Foreign Application Priority Data

Jul. 12, 2012  (JP) .................................. 2012/156074

(51) Int. Cl.
*G01N 23/00* (2006.01)
*G21K 7/00* (2006.01)

(52) U.S. Cl.
USPC ........... 250/310; 250/306; 250/307; 250/311; 250/492.3

(58) Field of Classification Search
USPC ................. 250/306, 307, 310, 311, 492.3
See application file for complete search history.

(56) References Cited

U.S. PATENT DOCUMENTS

| 5,493,116 | A | * | 2/1996 | Toro-Lira et al. | 250/310 |
| 7,449,690 | B2 | * | 11/2008 | Nishiyama et al. | 250/310 |
| 7,462,828 | B2 | * | 12/2008 | Fukada et al. | 250/310 |

FOREIGN PATENT DOCUMENTS

| JP | 09-507331 A | 7/1997 |
| JP | 2006-0228999 A | 10/2006 |
| JP | 2006-332038 A | 12/2006 |

* cited by examiner

*Primary Examiner* — Jack Berman
*Assistant Examiner* — Meenakshi Sahu
(74) *Attorney, Agent, or Firm* — McDermott Will & Emery LLP (57) ABSTRACT

The charged particle beam apparatus having an opening formation member formed with an opening for passage of a charged particle beam emitted from a charged particle source, and either a detector adapted to detect charged particles having passed through the passage opening or a detector adapted to detect charged particles resulting from bombardment on another member of the charged particles having passed through the opening, comprises an aligner for aligning charged particles discharged from the sample and a control unit for controlling the aligner, wherein the control unit controls the aligner to cause it to shift trajectories of the charged particles discharged from the sample so that length measurement may be executed on the basis of detection signals before and after the alignment by the aligner.

12 Claims, 9 Drawing Sheets

CHARGED PARTICLE BEAM APPARATUS

BACKGROUND OF THE INVENTION

The present invention relates to charged particle beam apparatuses and pattern measuring methods and more particularly, to a charged particle beam apparatus for aligning charged particles given off from a sample to detect them and a pattern measuring method therefor.

As a semiconductor pattern becomes corpuscular, a delicate difference in configuration has an influence upon operational characteristics in a device and accordingly, needs for management of configuration have been raised. Therefore, a scanning electron microscope (SEM) used for inspection and measurement of semiconductors has been required of high sensitivity and high accuracy than in the past more and more. Especially, highly efficient detection of signals given off from a bottom or the like of such a pattern of large aspect ratio (depth/width) as a deep hole or trench has been demanded.

In this case, how to detect efficiently a signal among discharged signals of less amounts is important and thus, making full use of discrimination of angle and direction of detection signals can be one of solving measures. JP-A-09-507331 discloses a SEM having two-stages of detectors adapted to discriminatively detect, for the sake of forming a high contrast mage of a hole bottom on the basis of electrons discharged from the bottom of such a deep hole as a contact hole, electrons passing through a trajectory close to the optical axis of an electron beam by having a small relative angle to the optical axis, that is, high angle electrons and electrons passing through a trajectory relatively distant from the optical axis of the electron beam by having a larger relative angle to the optical axis in contrast to the high angle electrons, that is, low angle electrons. Further, disclosed in JP-A-2006-228999 and JP-A-2006-332038 is a SEM having an aligner for secondary electrons adapted to control trajectories of secondary electrons with the aim of unifying signals detected by means of a plurality of detectors.

By selectively detecting electrons in the specified directions on the basis of angle discrimination as explained in the JP-A-09-507331, JP-A-2006-228999 and JP-A-2006-332038, an image emphasizing information indicative of the hole bottom or the like can be formed. Of the electrons discharged from the hole bottom, however, electrons discharged from a portion near the side wall have a high possibility of impinging upon the side wall and the efficiency of detection of them is lowered. Especially when outputs of the right and left detectors are attempted to be uniform as explained in JP-A-2006-228999 and JP-A-2006-332038, values of brightness at the left and right edges are unified in the case of an objective of a hole pattern and there is a possibility that a signal of one edge cannot be detected sufficiently. In particular, with a critical dimension-scanning electron microscope (CD-SEM) used, highly accurate measurement is difficult to realize unless both the two edges representing measurement references have each a high S/N ratio.

SUMMARY OF THE INVENTION

A charged particle beam apparatus and a pattern measurement method aiming at revealing information indicative of the edge of bottom of such a high-aspect structure as a deep hole and deep trench will be described hereinafter. In addition, a charged particle beam apparatus and a pattern measurement method which aim at discriminating a pattern which is difficult for judgment through the use of a top/down image.

To comply with the above object and cope with the above problem, according to one embodiment of the present invention, a charged particle beam apparatus having an opening formation member formed with an opening for passage of a charged particle beam emitted from a charged particle source, and either a detector for detecting charged particles discharged from a sample and having passed through the passage opening or a detector for detecting charged particles resulting from bombardment upon another member of the charged particles having passed through the passage opening, comprises an aligner for aligning the charged particles discharged from the sample and a control unit for controlling the aligner, wherein the control unit controls the aligner to cause it to shift trajectories of the charged particles discharged from the sample and length measurement or critical dimensioning is executed on the basis of detection signals before and after alignment by the aligner.

To comply with the above object and cope with the above problem, according to another embodiment of the invention, a charged particle beam apparatus having an opening formation member formed with an opening for passage of a charged particle beam emitted from a charged particle source, and either a detector for detecting charged particles discharged from a sample and having passed though the passage opening or a detector for detecting charged particles resulting from bombardment upon another member of the charged particles having passed through the passage opening, comprises an aligner for aligning the charged particles discharged from the sample and a control unit for controlling the aligner, wherein the control unit forms a signal waveform on the basis of an output of the detector, aligns the charged particles discharged form the sample such that a brightness indicated by a peak of the signal waveform satisfies a predetermined condition and executes length measurement of a pattern dimension on the sample by using a signal waveform obtained on the basis of the alignment.

To comply with the above object and cope with the above problem, according to still another embodiment of the invention, a charged particle beam apparatus having an opening formation member formed with an opening for passage of a charged particle beam emitted from a charged particle source and either a detector for detecting charged particles having discharged from a sample and passed though the passage opening or a detector for detecting charged particles resulting from bombardment upon another member of the charged particles having passed through the passage opening, comprises an aligner for aligning the charged particles discharged from the sample and a control unit for controlling the aligner, wherein the control unit judges a line and/or a space formed on the sample on the basis of a signal waveform detected after alignment by means of the aligner.

Advantageously, with the above construction, information indicative of the edge of bottom of a structure of high aspect such as a deep hole or deep trench can be revealed. Further, identification of a pattern whose judgment is difficult through a top/down image can be made possible.

DESCRIPTION OF THE EMBODIMENTS

In order to selectively detect charged particles given off in a specified direction, a detector or a secondary electron conversion electrode is considered to be arranged at a specified angle or in a specified direction. Employed as a principal method for angle/direction discrimination is a method using a plurality of detectors. But, the arrangement and number of the detectors limits the angle and direction effective for signal discrimination, making it difficult to carry out discrimination at arbitrary angles and/or in arbitrary directions.

To solve these difficulties, the use of an annular detector comprised of a plurality of detection elements is considerable. With the annular detector used, however, when the number of division of the elements is increased to provide flexibility in discrimination performance, the detection signal per element decreases. Further, errors in manufacture process of the apparatus will induce the possibility of degrading the accuracy of discrimination. The reduction in accuracy due to the manufacture error can be suppressed to some extent by using a secondary electron aligner but a sufficient signal quantity cannot sometimes be ensured.

A charged particle beam apparatus and a pattern dimension measuring method which can sufficiently maintain a signal based on charged particles discharged in a specified direction while excluding signals in other directions will be described in the following by making reference to the accompanying drawings. Especially, in the present embodiment, a charged particle beam apparatus and a pattern dimension measuring method will be described which can permit efficient angle discrimination excluding a signal quantity reduction per a detector and detection element and a shift of field of view as well by using a plurality of detectors or detection elements at the time that angles/directions of secondary electrons are discriminatively detected.

Of signals discharging from the sample, necessary information only is selectively detected, unnecessary signals are discarded as noises and charged particles discharged from the sample are aligned in an arbitrary direction by means of the aligner. By doing so, charged particles arriving at the detector are detected selectively in accordance with discharge angles. Particularly, by suppressing unnecessary information in signals discharged from a recess whose configuration is difficult to observe, useful information can be made conspicuous to permit execution of configuration inspection and the like.

More specifically, a restrictive member for selective passage of part of charged particles discharged from the sample is arranged and the aligner is so controlled as to perform switchover between a first alignment state for passing charged particles in a first discharge direction and a second alignment state for passing charge particles in a second discharge direction. Through this control, in an aligned status, information in a specified direction is emphasized but information in a direction other than the specified direction is limited. Namely, by changing the aligned status and by detecting signals before and after the change, a signal in each of the plural directions can be improved in S/N. Especially, in the CD-SEM for measuring dimensions among a plurality edges at different positions, its measurement accuracy can be improved.

According to the present embodiment, information around the bottom side wall of deep hole/deep trench (for example, edge information) can be detected with high accuracy and in the semiconductor manufacture process, for example, more accurate and effective process management can be ensured.

Figure 1:
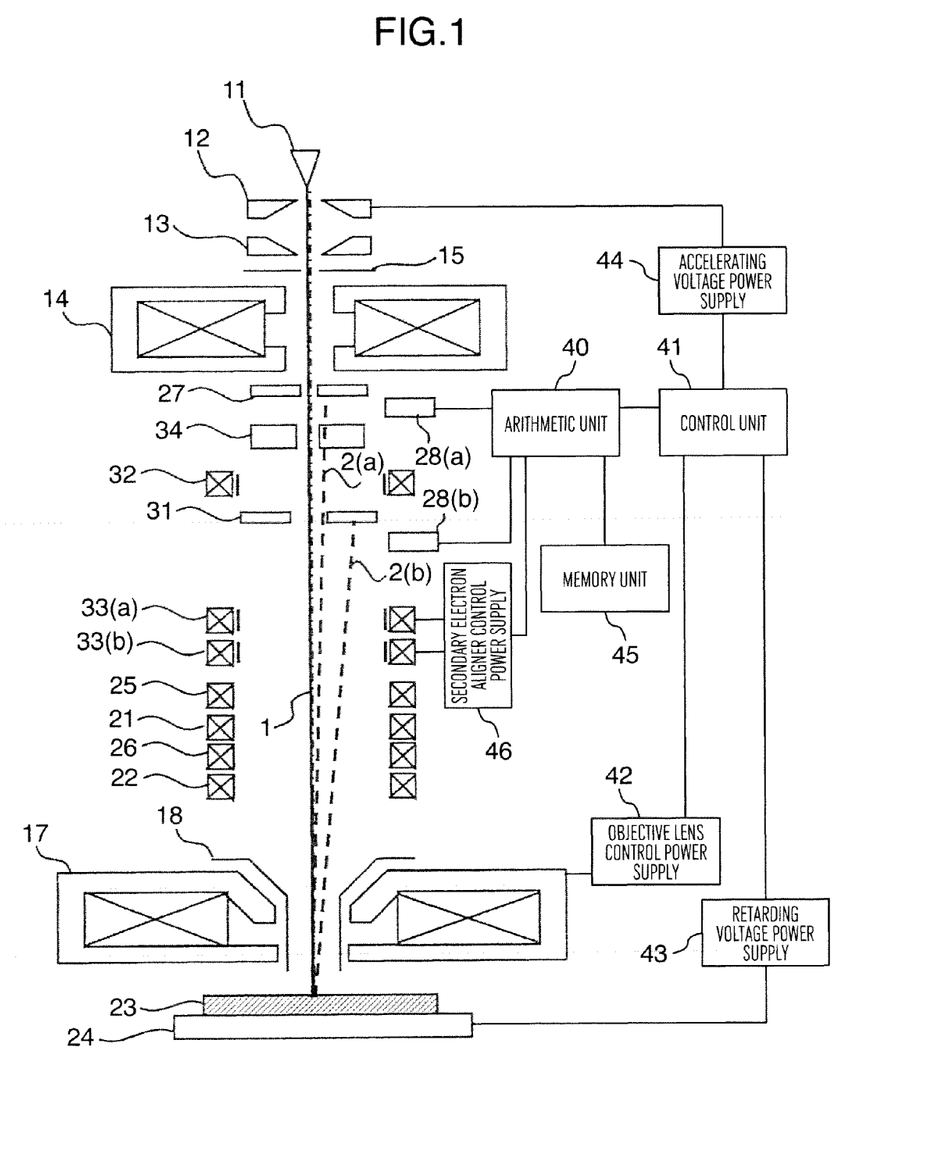
FIG. 1 is a diagram illustrative of the conceptual structure of a scanning electron microscope.

Referring now to FIG. 1, the conceptual structure of a scanning electron microscope will be described. By applying an extraction voltage 12 between an electric field emission cathode 11 and an extraction electrode 13, a primary electron beam 1 is extracted. The primary electron beam 1 undergoes a convergence action by means of a condenser lens 14 and a scanning deflection by means of an upper scan deflector 21 and a lower scan deflector 22. Deflection intensities the upper and lower deflectors 21 and 22 have are so adjusted as to cause the primary electron beam 1 to scan on a sample 23 two-dimensionally with respect to a fulcrum at the lens center of objective lens 17. Similarly, the primary electron beam is subject to deflection actions by upper and lower image shift deflectors 25 and 26 which are adapted to change the scanning position. The primary electron beam 1 subject to the deflection is further accelerated by means of an accelerating cylinder 18 arranged in a passage of the objective lens 17. The primary electron beam 1 undergoing further acceleration at the lower stage is focused by the lens action of objective lens 17, finally bombarding on the sample 23 held by a holder 24. Under irradiation of the primary electrons, secondary electrons are discharged from the surface of sample 23. The secondary electrons can be sorted into secondary electrons 2 (a) at high angles in directions parallel to the optical axis and secondary electrons 2 (b) at low angles representing low angle components in directions inclined towards the sample surface. The secondary electrons propagate along the optical axis inversely to the primary electrons and reach a secondary electron limit plate 31. The high-angle secondary electrons 2 (a) pass through a hole of the secondary electron limit plate 31 and bombard on a reflector 27 (conversion electrode), that is a member different from a detector so as to be converted into tertiary electrons which in turn are detected by mean of an upper detector 28 (a). A secondary electron aligner 32 does not align the electron beam but aligns the secondary electrons 2(a) selectively towards the reflector 27 in order that the secondary electron 2(a) can be prevented from passing though the electron beam pass opening and from directing towards the electric field emission cathode 11.

The secondary electrons 2 (b) at low angles impinge upon the secondary electron limit plate 31 and converted into tertiary electrons which in turn are detected by a lower detector 28 (b). Detected signals are processed by using an arithmetic unit 40. The signals detected by the individual detectors are converted into digital images. With a view to promoting an image S/N, the thus obtained images may be added and then imaged. A control unit 41 is connected to arithmetic unit 40, objective lens control power supply 42, retarding voltage power supply 43, accelerating voltage power supply 44, memory unit 45 and secondary electron aligner control power supply 46 so as to control operation of these components.

For the purpose of angle discrimination, the secondary electrons 2(a) at high angles must pass through the hole of secondary electron limit plate 31 but the trajectory of the secondary electrons will sometimes depart from the optical axis under the influence of the use of image shift and the passage through objective lens 17. Conversely, the hole of secondary electron limit plate 31 will sometimes be disposed at a site distant from the optical axis under the influence of accuracies of assemblage and optical axis adjustment or will sometimes be disposed distantly from the optical axis intentionally with the aim of selecting the hole diameter. Typically, the secondary electron aligner is used in order for the secondary electrons 2 (a) at high angles to be caused to constantly pass through the hole of secondary electron limit plate 31. By using lower and upper secondary electron aligners 33(b) and 33(a), the alignment of secondary electron trajectory is controlled. To avoid the influence upon the trajectory of primary electrons, a Wien filter comprised of electrodes and magnetic field coils is used as the secondary electron aligner.

Figure 2:
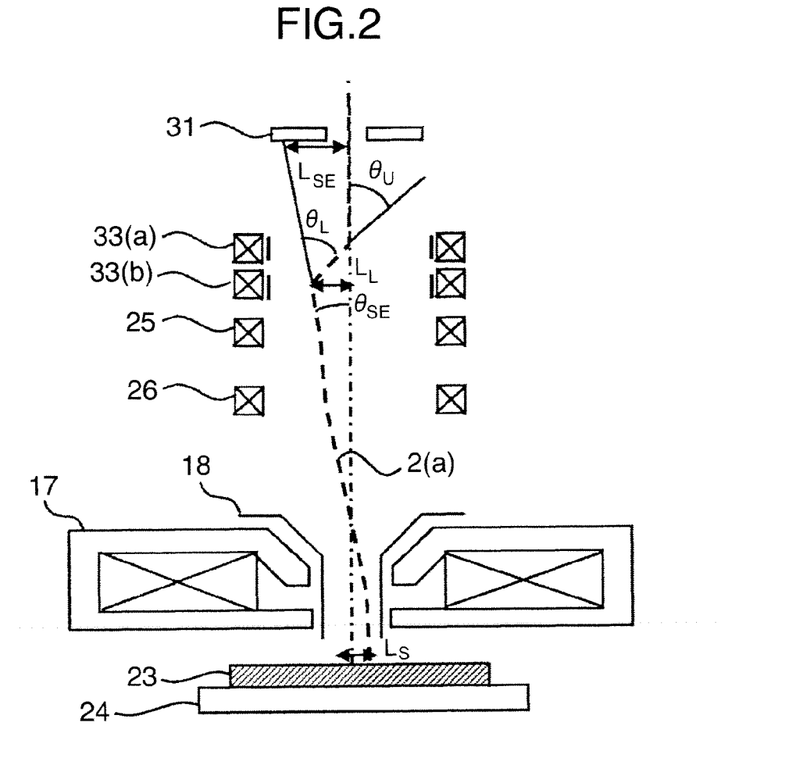
FIG. 2 is a diagram illustrating an example of a trajectory of a secondary signal aligned by means of a secondary signal aligner.

Turning to FIG. 2, the concept of a method for controlling the secondary electron aligners 33 (a) and 33 (b) will be explained. Through the use of image shift deflectors 25 and 26, the primary electron beam is irradiated on a spot Ls distant from the optical axis on the sample surface. Secondary electrons 2 (a) at high angles discharged therefrom propagate inversely along the optical axis. When passing through the objective lens 17 and image shift deflectors 25 and 26, the secondary electrons undergo action of deflection and enter the lower secondary electron aligner 33 (b) with an axis eccentricity $L_L$ and at an angle $\theta_{SE}$. Subsequently through the use of the lower secondary electron aligner 33 (b), the secondary electrons are so aligned at an angle $\theta_L$ as to be allowed to pass through the center of upper secondary electron aligner 33 (a). Next, by using the upper secondary electron aligner 33 (a), the thus aligned secondary electrons are so aligned at an angle $\theta_U$ as to be parallel to the optical axis, thus being permitted to pass through the center of secondary electron limit plate 31 in parallel with the optical axis.

The foregoing explanation has been given by making reference to the longitudinally sectional view in FIG. 2. When taking actual rotation due to the magnetic field in the objective lens 17, however, the secondary electrons need to be controlled also in azimuthal directions. At that time, rotational angles due to the magnetic field are determined in advance in connection with the individual components of azimuths in the individual secondary electron aligners and control operation is conducted through matrix operation. The rotational angles due to the magnetic field can be determined by using a secondary electron arrival position detecting method or electron trajectory simulation.

Figure 3:
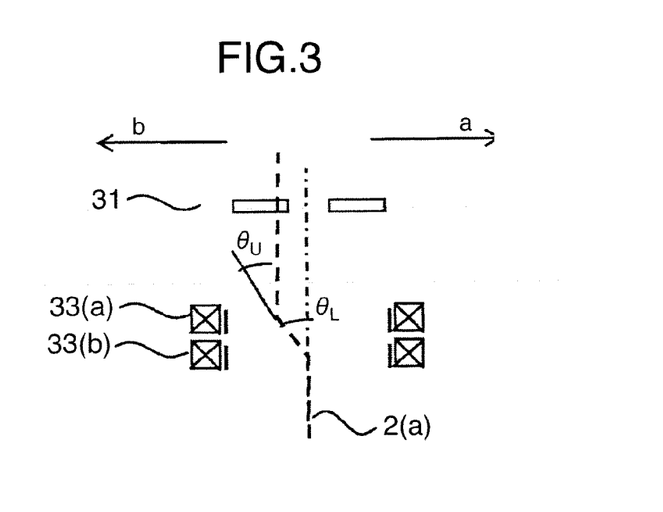
FIG. 3 is a diagram illustrating an example of an aligned trajectory of secondary electrons by means of the secondary electron aligner.

Next, a method for controlling alignment toward off-optical axis in the secondary electron limit plate 31 will be described with reference to FIG. 3. By controlling secondary electrons 2 (a) during non-use of image shift in such a manner that $\theta_L$, and $\theta_U$ are equal to each other and in opposite directions, only position of the trajectory can be shifted while the trajectory being kept to be parallel to the optical axis. In the present embodiment, this is utilized so that signals at desired angles of the high angle secondary electrons 2(a) may be passed through the hole of secondary electron limit plate 31 by controlling the position of arrival of the high angle secondary electrons 2 (a) at the secondary electron limit plate 31 through the use of the secondary electron aligner.

In addition, the present apparatus is also provided with the function to form a line profile on the basis of detected secondary electrons or reflected electrons. The line profile is formed on the basis of information indicative of an electron detection amount or brightness of a sample image which is obtained by scanning the primary electron beam linearly or two dimensionally and the thus obtained line profile is used for dimension measurement of a pattern formed on a semiconductor wafer, for instance.

The control computer has been described in connection with FIG. 3 as being integral with the scanning electron microscope or so correspondingly but this is by no means limited and procedures as will be described below may be conducted with a control processor arranged separately from the scanning electron microscope. In that case, it is necessary to provide transmission media for transmitting a detection signal detected by the secondary signal detector 13 to the control processor and for transmitting signals from the processor to the lens and aligner of the scanning electron microscope and to provide an input/output terminal for inputs/output of signals transmitted by way of the aforementioned transmission media.

In embodying the present invention as described below, a method and an apparatus therefor will be described in which only charged particles discharged in specified directions are detected by aligning secondary electrons discharged from a scanning spot by means of the secondary electron aligner without changing the incidence on the spot of a charged particle beam vertical to a substrate normally used, by inducing a profile of the detected signal and by detecting a corpuscular configuration of a pattern on the basis of the profile. While the present invention can be applicable to various kinds of charged particle beam apparatuses (SEM, FIB and so on), an example using a SEM as a typical apparatus will be described.

Embodiment 1

In this embodiment, corpuscular configurations in deep trench/hole will be taken up. A deep trench pattern is diagrammatically illustrated at (a) in FIG. 4. When a deep trench pattern is observed with the normal SEM, a signal generating from the bottom of a hole is shielded by the side wall and hardly detected, with the result that its signal amount is decreased as compared to that from the upper portion of hole, producing an image and profile as shown at (b) in FIG. 4. Under this condition, however, the shape of trench bottom cannot be confirmed and accordingly, the whole of signal amounts from the trench bottom is increased typically by an expedient of raising the pre-charge or intensifying the electric field. With the signal amounts increased, the trench bottom configuration can be confirmed correspondingly easily but this is insufficient in many cases. Accordingly, by using the present method, selective detection of signals is carried out. Firstly, secondary electrons are curved toward a direction a in FIG. 3 by means of the SE aligner so that an image and a signal profile as shown at (c) in FIG. 4 may be obtained. Subsequently, when the secondary electrons are curved toward a direction b in FIG. 3, an image and a signal profile as shown at (d) in FIG. 4 can be obtained. As a result, at the bottoms of right and left side walls of the deep trench pattern shown at (a) in FIG. 4, the presence of a corpuscular configuration 102 of bottom failing to be detected at (b) in FIG. 4 can be detected.

Figure 4:
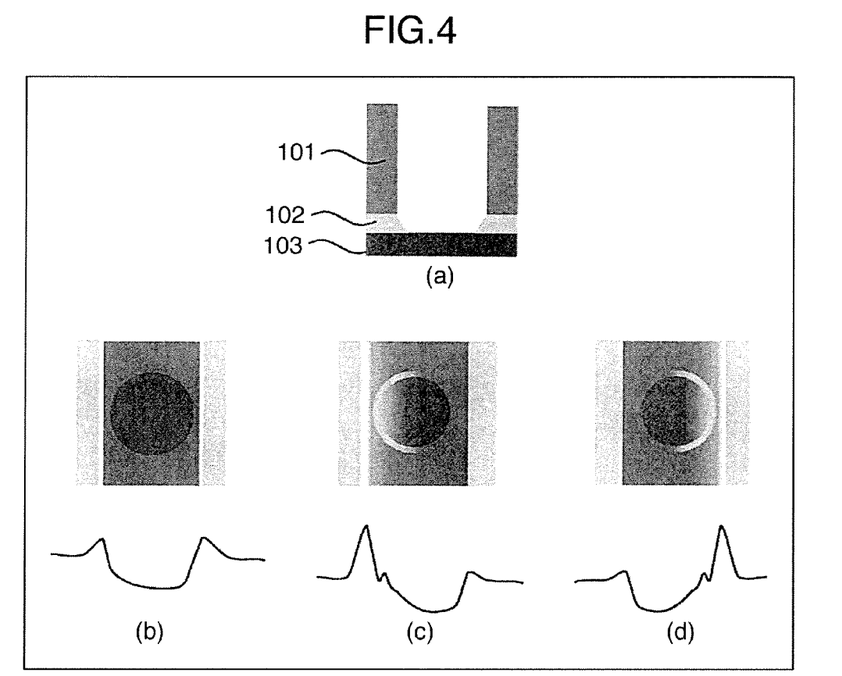
FIG. 4 is a diagram illustrative of the effects by the alignment of secondary electrons.

Since the SE aligner can be so operated as to be set in arbitrary direction and at arbitrary angle, even for a hole configuration having an edge through 360 degrees as shown at (a) in FIG. 4, bottom observation in all directions of edge can be permitted. Further, the SE aligner can be controlled by the application of only voltage and current so as to operate rapidly and therefore, a drift of the field view can be prevented during right/left switchover, thus ensuring that the SE aligner can be applied without decreasing the throughput even in the automated process.

Figure 6:
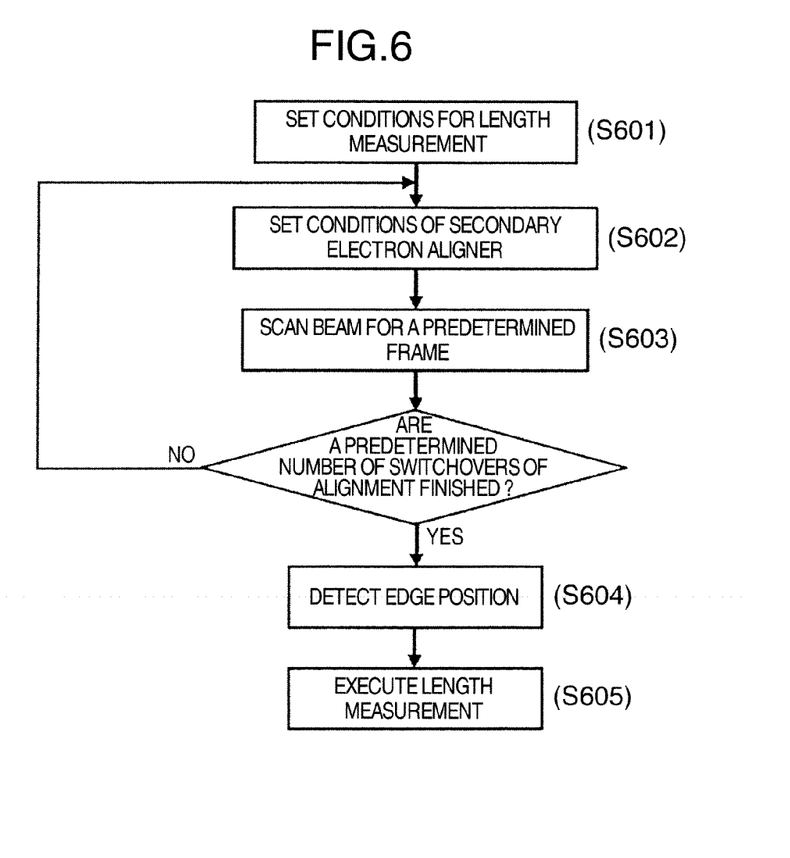
FIG. 6 is a flowchart showing procedures of length measurement carried out by using a signal waveform obtained on the basis of secondary electron alignment.
Figure 9:
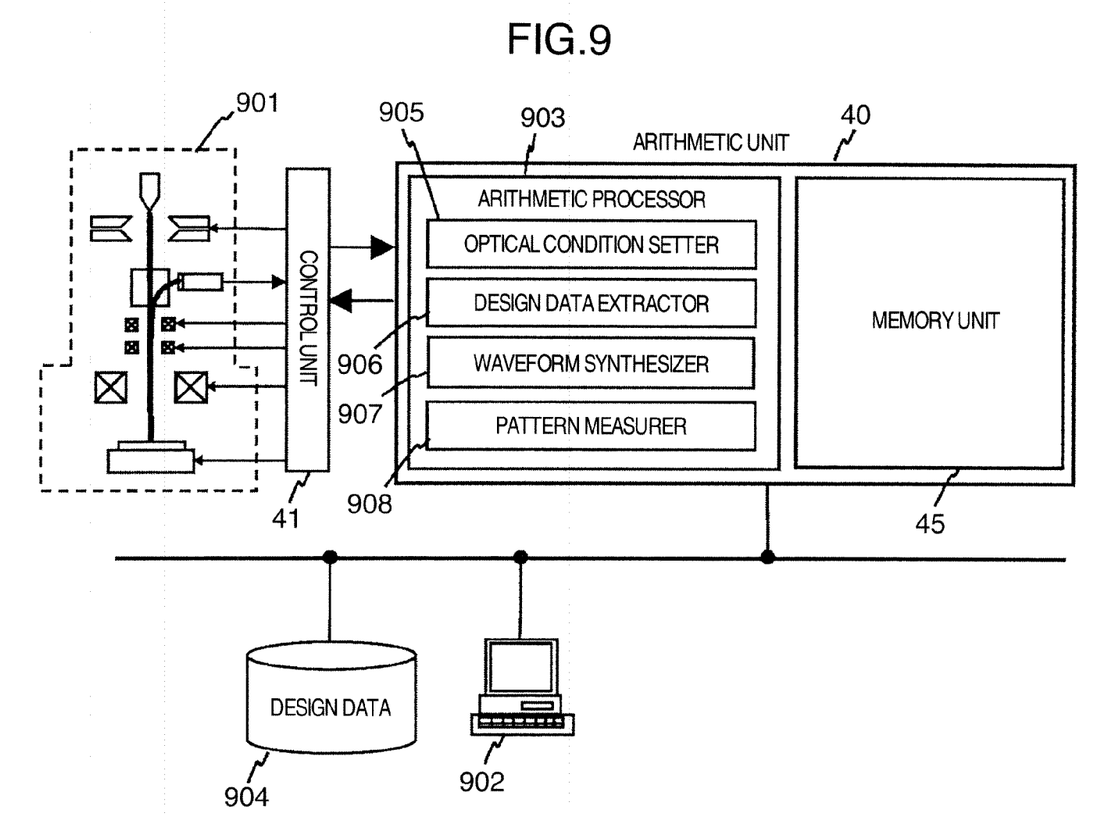
FIG. 9 is a diagram illustrative of conceptual configuration of a measuring system including the scanning electron microscope.
Figure 10:
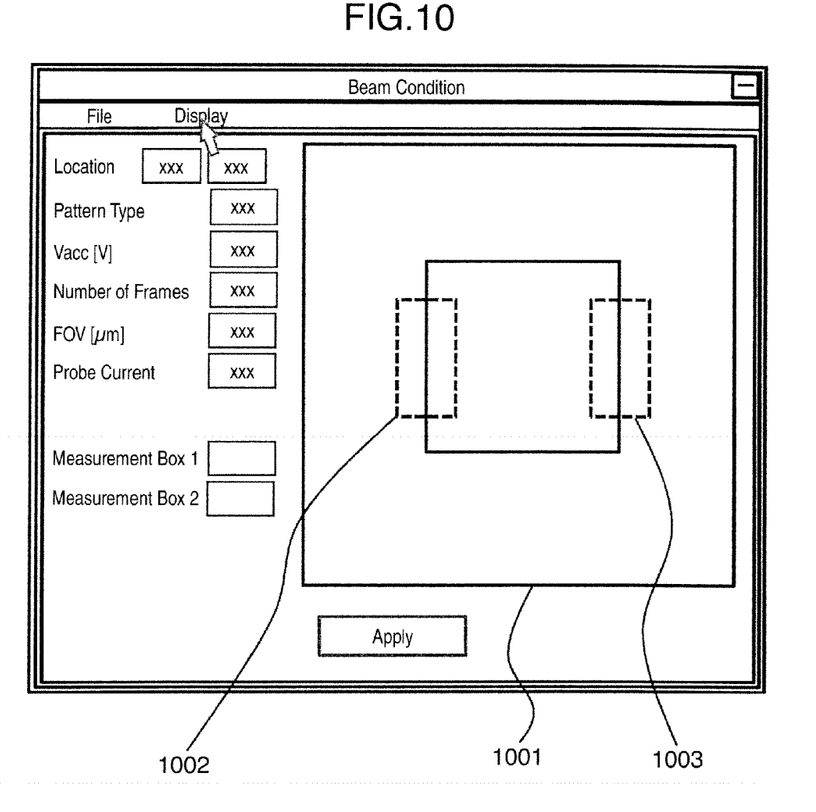
FIG. 10 is a diagram illustrating an example of a GUI screen adapted to set measurement conditions.

Turning now to FIG. 6, a flowchart is illustrated showing procedures for execution of dimension measurement on a sample on the basis of control of a position where secondary electrons reach by the action of the secondary electron aligner. Firstly, measurement conditions of a pattern are set from an input unit connected to the arithmetic unit 40 in step 601. Illustrated in FIG. 9 is an example of a measurement system in which the input unit 902 for setting the measurement conditions is coupled to the measurement apparatus including a scanning electron microscope 901 by way of a network. In FIG. 10, an example of screen of a GUI (Graphical User Interface) for measurement condition setting to be displayed on a display of input unit 902. In the GUI screen, conditions for measurement using an electron beam (for example, optical conditions of an electron beam) can be set. On the basis of the optical conditions set therein, an optical condition setter 905 sets conditions for control by the control unit 41 and setting information thereof is stored in the memory unit 45. On the basis of these conditions, conditions for controlling the sample stage and the deflectors adapted to adjust the positions of field of view.

On the basis of inputs of coordinate information (location) and size of field of view (FOV size), a design data extractor 906 of an operation processor 903 built in the arithmetic operation unit 40 reads design data of the coordinates out of a design data medium 904 and displays it as figure data in a display area 1001. Along with optical conditions of the electron beam, length measurement boxes 1002 and 1003 indicative of measurement references (measurement start point and end point) of a measurement objective pattern are also set in the display area 1001. On the basis of detection of a predetermined brightness portion or a peak top, a pattern measurer 908 sets a measurement start point and a measurement end point in the length measurement boxes 1002 and 1003 and measures a dimension between the two points.

Figure 8:
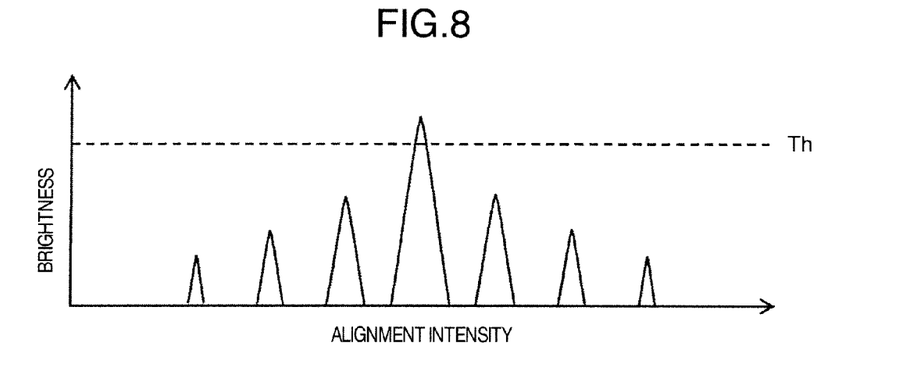
FIG. 8 is a graphic representation indicating changes in brightness of peaks when the secondary electron alignment condition is changed.

Next, the optical condition setter 905 sets conditions for secondary electron aligners in accordance with the set measurement box position and on the basis of setting conditions stored in a memory 45 (step 602). As the conditions for secondary electron aligners, secondary electron alignment conditions are selected which can sufficiently assure brightness of edges contained in the measurement box. When secondary electron alignment conditions are stored in advance according to measurement conditions, two alignment conditions necessary for measurement are read out of the memory unit 45. In addition, in the event that proper alignment conditions are unknown, the secondary electron trajectory may be aligned in the measurement direction in a unit of predetermined alignment intensity and a signal waveform may be selected which occurs when a peak indicative of the edge becomes a predetermined value or more. Illustrated in FIG. 8 is a graph illustrating how the brightness shifts in response to alignment intensities of the plural secondary electron aligners in respect of a right or left edge of a hole. For the brightness at the edge portion being low (for example, a status at (b) in FIG. 4) and the brightness at the edge portion being high (for example, a statuses at (c) and (d) in FIG. 4), pieces of information can be obtained for both the statuses and therefore, measurement may be conducted by using signal waveforms obtained under such conditions for alignment that the brightness is the highest or the brightness is higher than a predetermined value. Alternatively, an approximation function passing through the peak position may be prepared and a peak position may be identified on the basis of the approximation function.

Since, in the case of a hole-pattern, conditions for proper alignment are different for the right and left edges, peak extraction based on selection of two proper alignment conditions selected from a plurality of choices is carried out. Further, when a space between lower-layer and upper-layer patterns is to be measured, clarification of one edge position of the lower pattern is sufficient and therefore, only one alignment condition may be set.

Figure 7:
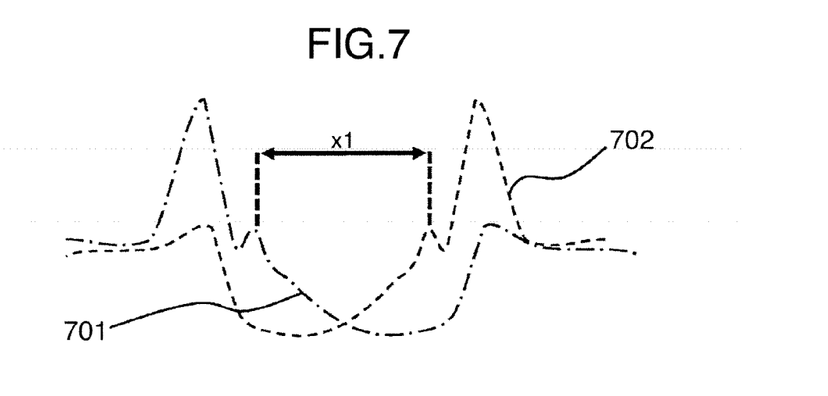
FIG. 7 is a diagram illustrating an example of superimposition of two signal waveforms obtained under different secondary electron alignments.

Next, under one or plural conditions for alignment of secondary electrons, the beam scanning based on the set optical conditions is carried out to form signal waveforms or images (step 603). In this step, beam scanning is conducted in accordance with setting of frame number (number of frames) exemplified in FIG. 10. When the secondary election alignment conditions are known in advance, images or signal waveforms are formed in accordance with the number of edges representing measurement reference but when the secondary electron alignment conditions are unknown, secondary electron alignment conditions of predetermined alignment intensity are set and images or signal waveforms are formed in accordance with the thus set individual conditions. After the processing, edge positions are detected and dimension measurements among the plural edges are executed (steps 604 and 605). For example, in the dimension measurement, a waveform 701 emphasized in a left edge and a waveform 702 emphasized in a right edge are selected and superimposed on each other by means of a waveform synthesizer 902 and a dimension between desired edges (x1 in the case of FIG. 7) is measured by means of the pattern measurer 908. Theoretically, the secondary electron aligner does not align the electron beam emitted from the cathode and so, fields of view used for acquisition of the waveforms 701 and 702 are quite the same. Accordingly, by superimposing the obtained waveforms each other in such a manner that their end positions are coincident, for example, a relative position between the two edges can indicate a distance between edges of an actual pattern and highly accurate dimension measurement can be accomplished.

Figure 11:
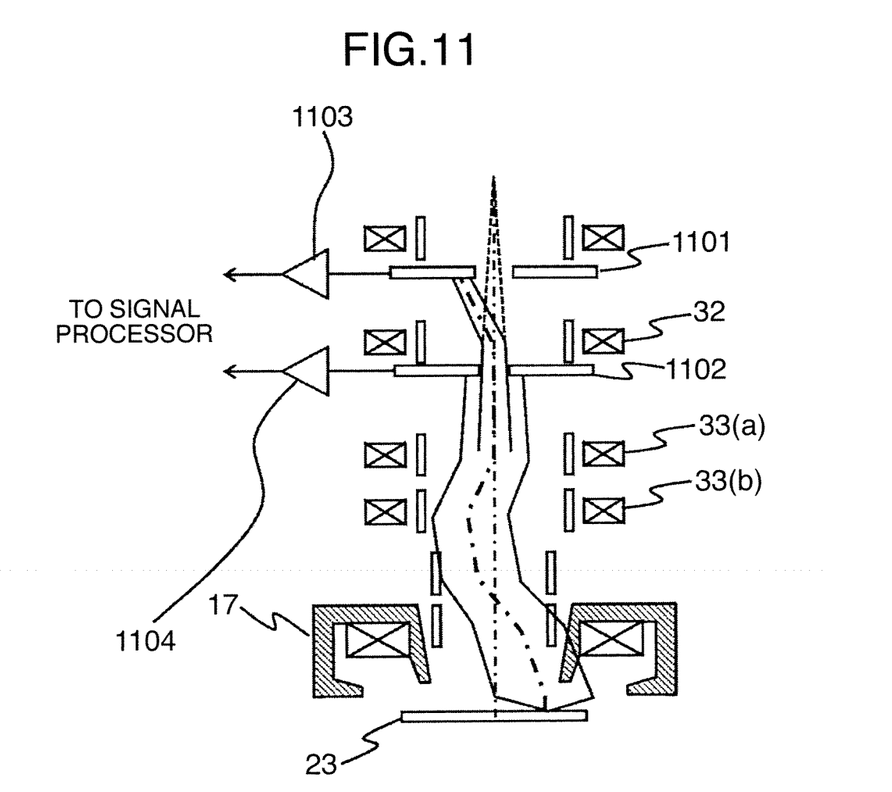
FIG. 11 is a diagram illustrating an example of the scanning electron microscope using a multichannel plate as the detector.

The foregoing embodiment has be explained by way of example of pattern dimension measurement conducted by using the secondary electron aligners built in the scanning electron microscope exemplified in FIG. 1 but the dimension measurement may be carried out by using a scanning electron microscope as exemplified in FIG. 11, for instance. The scanning electron microscope in FIG. 11 comprises a detector including, instead of the reflection plates 27 and 31 in FIG. 1, micro-channel plates 1101 and 1102 adapted to directly detect electrons the present example, the micro-channel plate 1102 substitutes for the opening formation member having an electron beam passage opening. Signals detected by the micro-channel plates 1101 and 1102 are amplified by amplifiers 1103 and 1104, respectively, and transmitted to a signal processing unit not shown.

The scanning electron microscopes exemplified in FIGS. 1 and 11 comprise detectors for detecting electrons at low angles (namely, lower detector 28 (b) and micro-channel plate 1102). In the foregoing embodiment, the alignment is effected such that the trajectory of secondary electrons are positioned at a proper spot in relation to the member for limiting the passage of electrons at low angles and an example has been explained in which proper alignment conditions are determined on the basis of a change in upper-side detection signal but the alignment condition may be found out on the basis of the output of lower detector. In the example of FIG. 8, on the basis of the output of the upper side detector, an alignment intensity is determined at which the brightness of a specified edge is the highest but in contract to the maximization of the output at the upper detector, minimization of the output of the lower detector may be considered. Accordingly, on the basis of the output of the lower detector, conditions for alignment may be determined Embodiment 2

Embodiment 2 is directed to LS judgment

Figure 5:
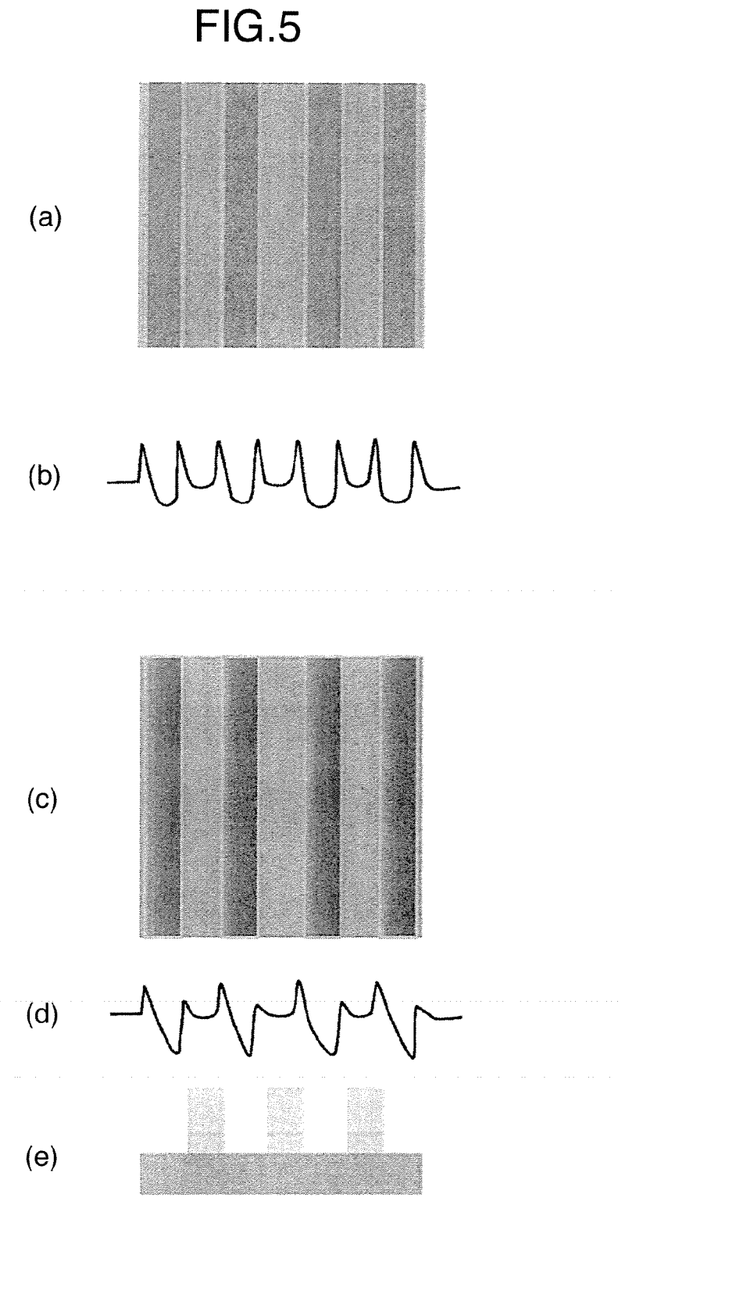
FIG. 5 is a diagram also illustrative of the effects by the alignment of secondary electrons.

An example of line and space image in the ordinary SEM is illustrated at (a) in FIG. 5. When the line and space are equal in size and a difference in clearness is mall therebetween, the profile becomes as shown at (b) in FIG. 5 and the line and space are difficult in discriminating from each other. According to the present invention, however, a space portion can be shaded as shown at (c) in FIG. 5 by aligning secondary electrons in a direction a in FIG. 3, making it easy to judge a concave/convex configuration. A component of angle of elevation of discharging secondary electrons is different at the line portion from that at the space portion. Since secondary electrons emitting from the space portion will shield secondary electrons the adjoining line pattern generates, the range of elevation angles at which discharging is possible is limited by the width of space and the height of line pattern and consequently, almost secondary electrons are of high angle components. Accordingly, these secondary electrons are more sensitive to the detection signal control using the SE aligner and secondary electron limit plate than those from the line portion, so that an image having a shade is formed at the space portion as shown at (c) in FIG. 5. At that time, the line can be discriminated from the space from a difference in profile between the line portion and the space portion. For the above reasons, the space portion is caused to have a asymmetrical brightness after the alignment. Consequently, as shown at (d) in FIG. 5, the gradient of profile at the space portion becomes larger than that at the line portion. By making full use of this, the concave/convex configuration can be judged to determine that the image at (a) in FIG. 5 corresponds to a configuration at (e) in FIG. 5.

More specifically, since the signal after alignment becomes different depending on whether the peak generates from an interval "line to space" or "space to line", the concave/convex configuration is judged by extracting the feature of the peak. For example, as shown at (d) in FIG. 5, it can be understood that when the alignment direction is as shown exemplarily at "a" in FIG. 3, the space exists in the alignment direction of high peak and the line exists oppositely to the alignment direction. It can be seen that the space exists in a direction of a peak having its skirt spreading and the line exists in a direction opposite to the alignment direction. It also can be seen that the line exists in an alignment direction of low peak and the space exists in a direction opposite to the alignment direction. Then, it can be seen that in an alignment direction of a peak having its skirt portion becoming narrow, the line exists in the alignment direction of peak and the space exists in a direction opposite to the alignment direction. Further, in the case of the alignment direction being "b" in FIG. 3, results inverse to those in direction "a" in FIG. 3 can be obtained.

Preferably, by determining changes in peak as described above on the basis of comparison, for example, between signal waveforms before and after the alignment, between a signal waveform without alignment and a signal waveform with alignment or between signal waveforms with alignment (comparison between a plurality of signal waveforms obtained through alignment in inverse directions, for instance), line or space may be judged. In addition, by comparing adjoining peaks contained in a signal waveform after alignment, the aforementioned features may be extracted.

On the basis of the judgment reference as above, the arithmetic operation unit 903 makes a decision as to whether a region surrounded by two peaks is a line or a space. Advantageously, the secondary electron aligner does not deflect the primary electron beam and therefore, a waveform required for measurement and a relative position of a waveform for concave/convex configuration judgment do not change, thereby ensuring a highly accurate judgment without misunderstanding the judgment results. By executing the secondary electron alignment continuously and making the aforementioned concave/convex judgment without performing movement of the stage or shift of field of view by the deflector before or after beam scanning for measurement, the aforementioned effects can be obtained. To add, after differentiating a signal waveform to make features of waveform clear, the concave/convex configuration judgment may be carried out. Further, by using the signal waveforms after alignment, both the judgment and measurement of the concave/convex configuration may be executed. In this case, a pattern can be measured by using a signal waveform in which a peak of an edge portion is revealed.

According to the present embodiment, even for a pattern having continuous similar configurations and being hardly judged by only its feature of waveform such as the line and space in a SEM image, the height information can be utilized and more accurate concave/convex configuration judgment can therefore be assured. Further, since the incident electrons are not slanted and besides, the stage is not inclined, amendment for a drift of field of view is not necessary, having a small influence upon the throughput and present invention is effective even in the automated production process. In addition, the alignment of secondary electrons can be conducted in all directions to cause both a longitudinal pattern and a transverse pattern to be treated and besides, not only even a linear configuration such as a simple line and space but also a two-dimensional pattern having longitudinal and transverse edges can be judged.

The invention claimed is:

1. A charged particle beam apparatus having an opening formation member formed with an opening for passage of a charged particle beam emitted from a charged particle source, and either a detector adapted to detect charged particles emitted from a sample and having passed through said passage opening or a detector adapted to detect charged particles resulting from bombardment on another member of the charged particles having passed through said passage opening, comprising:
   an aligner for aligning charged particles emitted from said sample and a control unit for controlling said aligner, wherein said control unit controls the aligner to cause it to shift trajectories of the charged particles emitted from said sample so that length measurement may be executed on the basis of detection signals before and after the alignment by said aligner.

2. A charged particle beam apparatus according to claim 1, wherein said aligner is a Wien filter.

3. A charged particle beam apparatus according to claim 1, wherein said control unit changes the alignment status of said aligner into at least two statuses and the length measurement is executed by using signal waveforms obtained in said two alignment statuses.

4. A charged particle beam apparatus according to claim 1, wherein said control unit executes the length measurement by using one of signal waveforms obtained when the alignment condition of said aligner is changed in plural manners, said one signal waveform having a peak height which satisfies a predetermined condition.

5. A charged particle beam apparatus according to claim 1, wherein said another member is a conversion electrode adapted to generate electrons under bombardment of charged particles emitted from said sample.

6. A charged particle beam apparatus according to claim 1, wherein said control unit selects an alignment direction by said aligner in accordance with a direction of said length measurement.

7. A charged particle beam apparatus having an opening formation member formed with an opening for passage of a charged particle beam emitted from a charged particle source, and either a detector adapted to detect charged particles emitted from a sample and having passed through said passage opening or a detector adapted to detect charged particles resulting from bombardment on another member of the charged particles having passed through said passage opening, comprising:
an aligner for aligning charged particles emmited from said sample and a control unit for controlling said aligner, wherein said control unit forms a signal waveform on the basis of an output of said detector, aligns charged particles emmited from said sample such that a brightness a peak of said signal waveform shows satisfies a predetermined condition, and executes length measurement of a pattern dimension on said sample by using a signal waveform obtained on the basis of said alignment.

8. A charged particle beam apparatus according to claim 7, wherein said aligner is a Wien filter.

9. A charged particle beam apparatus according to claim 7, wherein said control unit executes said length measurement by using a peak top of a signal waveform obtained when the alignment status of said aligner is changed by plural times or a peak having a brightness of a predetermined value or more.

10. A charged particle beam apparatus according to claim 7, wherein said another member is a conversion electrode adapted to generate electrons under bombardment of charged particles emitted from said sample.

11. A charged particle beam apparatus according to claim 7, wherein said control unit selects an alignment direction by said aligner in accordance with a direction of said length measurement.

12. A charged particle beam apparatus having an opening formation member formed with an opening for passage of a charged particle beam emitted from a charged particle source, and either a detector adapted to detect charged particles emitted from a sample and having passed through said passage opening or a detector adapted to detect charged particles resulting from bombardment on another member of the charged particles having passed through said passage opening, comprising:
an aligner for aligning charged particles emitted from said sample and a control unit for controlling said aligner, wherein said control unit judges a line and/or space formed on sample on the basis of a signal waveform detected after alignment by means of said aligner.

* * * * *